United States Patent
Kirschner et al.

(12) 
(10) Patent No.: US 6,261,600 B1
(45) Date of Patent: Jul. 17, 2001

(54) FOLIC ACID SUPPLEMENT

(75) Inventors: Mitchell I. Kirschner; George Paradissis, both of St. Louis; R. Saul Levinson, Chesterfield, all of MO (US)

(73) Assignee: DrugTech Corporation, Wilmington, DE (US)

( * ) Notice: Subject to any disclaimer, the term of this patent is extended or adjusted under 35 U.S.C. 154(b) by 0 days.

(21) Appl. No.: 09/303,000

(22) Filed: Apr. 30, 1999

(51) Int. Cl.[7] ............... A61K 9/46; A61K 9/16; A61K 31/4985
(52) U.S. Cl. ............ 424/466; 424/441; 424/489; 514/249
(58) Field of Search .................. 424/464, 439, 424/440–41, 466, 489; 446/5; 514/249

(56) References Cited

U.S. PATENT DOCUMENTS

| | | | |
|---|---|---|---|
| 4,710,387 | 12/1987 | Uiterwaal et al. | 426/72 |
| 4,752,479 | 6/1988 | Briggs et al. | 424/472 |
| 4,952,402 | 8/1990 | Sparks et al. | 424/419 |
| 5,028,411 | 7/1991 | Callingham et al. | 424/45 |
| 5,312,626 | * 5/1994 | Gergely et al. | . |
| 5,494,678 | 2/1996 | Paradissis et al. | 424/439 |
| 5,527,542 | 6/1996 | Serpelloni et al. | 424/488 |
| 5,569,477 | 10/1996 | Nesbitt | 426/5 |
| 5,587,172 | * 12/1996 | Cherukuri et al. | 424/401 |
| 5,733,575 | 3/1998 | Mehra et al. | 424/480 |
| 5,997,915 | * 12/1999 | Bailey et al. | . |

OTHER PUBLICATIONS

*Current Pediatric Diagnosis and Treatment,* 13th Ed., 1997.
*Current Obstetrics and Gynecology Diagnosis and Treatment,* 8th Ed., 1994.
*Physicians Desk Reference for Nonprescription Drugs (PDR),* 9th Ed., 610, 1988.
*Physicians Desk Reference for Nonprescription Drugs (PDR),* 9th Ed., 611, 1988.
*Physicians Desk Reference for Nonprescription Drugs (PDR),* 9th Ed., 705, 1988.
*Physicians Desk Reference for Nonprescription Drugs (PDR),* 9th Ed., 718, 1988.
*USP DI™ Drug Information for the Health Professional,* 18th Ed., 1998.
Whitney, E. and Rolfes, S., *Understanding Nutrition,* 6th Ed., 311–314, 1993.

* cited by examiner

*Primary Examiner*—Edward J. Webman
(74) *Attorney, Agent, or Firm*—Nath & Associates PLLC; Gary M. Nath; Joshua B. Goldberg

(57) ABSTRACT

The present invention is directed to novel chewable or dissolvable nutritional supplements for improving the absorption of folic acid in humans and other animals and methods of using said supplements. The nutritional supplements contain folic acid and non-toxic acid neutralizing alkaline compounds in chewable or dissolvable forms.

48 Claims, No Drawings

FOLIC ACID SUPPLEMENT

BACKGROUND OF THE INVENTION

1. Field of the Invention

The present invention is directed to novel chewable or dissolvable nutritional supplements in improved forms that optimize absorption of folic acid in humans and other animals, and methods of using said supplements. The nutritional supplements are formulated with folic acid and non-toxic acid neutralizing alkaline compounds in chewable or dissolvable forms which provide highly absorbable or highly bioavailable forms of folic acid.

2. Description of the Related Art

Folic acid deficiency is the most common vitamin deficiency experienced by individuals in the U.S. See *USP DI™ Drug Information for the Health Care Professional*, 18$^{th}$ Ed., 1988. It is crucial that an adequate level of folic acid be maintained in the body because folic acid plays an especially important physiological role. Folic acid, also known as pteroylglutamic acid and vitamin $B_9$, plays an important role in cell division, erythropoiesis and protein synthesis, all of which are processes very important to growing tissues. Folic acid is part of an enzyme complex that changes vitamin $B_{12}$ into its active form and helps synthesize amino acids into the new DNA required for dividing cells. See Whitney, E. and Rolfe, S., *Understanding Nutrition*, 6$^{th\ Ed.,}$ 311 (1993). Folic acid delivered to the body in food is often bound to glutamic acid, but the body prefers to absorb the folic acid in its "free" state. Therefore, folic acid has a low bioavailability. Id.

In fact, only about half of dietary folic acid is available to the body. The Recommended Daily Allowance (RDA) for folic acid takes this low bioavailability into account. For example, in the U.S., the RDA for folic acid is as follows: 150–200 mcg for adult males, 150–180 mcg for adult females, 400 mcg for pregnant females, 260–280 mcg for lactating women and 25–50 mcg for infants and children. See *Current Pediatric Diagnosis and Treatment*, 13$^{th}$ Ed., 1997.

Uncooked green vegetables, beans, liver, kidney, yeast, potatoes, cereal, mushrooms and fruit juices are all sources of folic acid. However, the heating of foods will destroy up to 90% of the bioavailable folic acid. See Whitney, E. and Rolfes, S., *Understanding Nutrition*, 6$^{th}$ Ed., 314 (1993). Therefore, natural sources of folic acid provide a low bioavailable or poorly absorbable form of folic acid.

Various internal and external factors can result in folic acid deficiencies in both males and females. For example, folic acid deficiency can occur when there is a need for increased cell proliferation, such as that experienced during pregnancy, cancer, blood loss and skin diseases. Folic acid is also very vulnerable to interactions with drugs. Drugs with similar chemical structures to folic acid, can replace folic acid in metabolic pathways. For example, aspirin, antacids, cholestyramine, anticonvulsants and oral contraceptives may interfere with the levels of folic acid in body tissues. Various other factors can also negatively impact folic acid levels, for example, smoking and prolonged stress. Id. at 313.

Further, folic acid is converted into an active form in the lever and is absorbed by the intestinal system. As a result, folate metabolism is vulnerable to any intestinal system disturbance, such as injury to GI tract cells or alcohol abuse. Id.

Regardless of the cause, folic acid deficiency carries serious consequences. Specifically, folic acid deficiency impairs cell division and protein synthesis. Further, folic acid deficiency slows the replacement of red blood cells and GI tract cells. A significant symptom of folic acid deficiency is anemia, including megaloblastic anemia and macrocytic anemia. Id.

The physiological demands for folic acid are elevated when additional stresses are placed upon the body. For instance, due to the increase in cell proliferation during a pregnancy, pregnant women require more folic acid than normal, and are at a greater risk for a folic acid deficiency. Therefore, the recommended intake of folic acid is increased during pregnancy. In view of this increased risk, physicians generally recommend that pregnant women supplement their diet with vitamin and mineral formulations. Folic acid supplementation during pregnancy is believed to reduce the risk of neural tube defects, such a spina bifida, in infants. See *Current Obstretics and Gynecology Diagnosis and Treatment*, 8$^{th}$ Ed., 1994. Other teratogenic effects (e.g. birth defects) are linked to underexposure to folic acid or overexposure to folic acid antagonists. See *Current Pediatric Diagnosis and Treatment*, 13$^{th}$ Ed., 1997.

Various approaches to increasing the bioavailability of folic acid have been described. Further, numerous approaches for reducing the risk of neural tube defects and other birth defects have also been described in several references.

For example, Nesbitt, U.S. Pat. No 5,569,477, discloses a chewing gum containing various vitamins and minerals, including folic acid. The vitamins and minerals are preferably present in levels prescribed by the U.S. RDA.

Serpelloni et al., U.S. Pat. No. 5,527,542, disclose a process for coating the surface of vitamin and other pharmaceuticals products with Maltitol sugar, to improve the taste and aesthetic appearance of the product. Whether in tablet or form, the products would be intended to be swallowed whole.

Sparks et al., U.S. Pat. No. 4,952,402, disclose a controlled release powder made of microparticles containing an active ingredient, such as vitamins or pharmaceuticals, and a polymer. The powder can be suspended in liquid and maintain its controlled release characteristics for a sustained period of time.

Callingham et al., U.S. Pat. No. 5,028,411, disclose a composition for the buccal or nasal administration of iron, zinc or folic acid to the body. The buccal and nasal sprays and lozenges of this invention are made of a neutral iron(III) complex, which is more effective in the neutral pH of the mouth and nose than in the gastrointestinal tract.

Mehra et al., U.S. Pat. No. 5,733,575, disclose a non-toxic enteric film coating for pharmaceuticals comprising a polymer, a detackifier, a viscosity modifier and an alkalizing agent. The coating prevents the active ingredient from being absorbed by the body until it reaches the intestines.

Briggs et al., U.S. Pat. No. 4,752,479, describe a multi-vitamin and mineral supplement for oral administration containing divalent calcium and magnesium as well as iron. The mineral supplement is adapted to be released in the upper gastrointestinal tract, while the iron component is adapted to be released in the lower intestinal tract.

Vitamin supplements for pregnant women containing folic acid have also been described in various references. Uterwaal et al., U.S. Pat. No. 4,710,38, describe a nutritional supplement for pregnant and breast-feeding women based on milk constituents containing, among other vitamins and minerals, folic acid.

Paradissis et al., U.S. Pat. No. 5,494,678, disclose a multi-vitamin and mineral supplement for pregnant women comprising a regimen of calcium, vitamin D and certain B complex vitamins, including folic acid. This supplement is tailored to maximize fetal development and maternal health during pregnancy.

The Physician's Desk Reference for Nonprescription Drugs describes various vitamin and mineral supplements which contain folic acid. For example, One-A-Day® Maximum Formula Vitamins and Minerals for Adults, made by Miles, Inc., is a multi-vitamin and mineral supplement indicated as a dietary pill to be swallowed once a day. The supplement contains 0.4 mg of folic acid. See *Physician's Desk Reference for Nonprescription Drugs*, 611 (9$^{th}$ Ed., 1988).

vitamins for Women, made by Vitamins for Women, Inc., is a set of vitamin and mineral supplements, one to be taken during the day and the other at night. The supplements contain 400 mcg of folic acid. See *Physician's Desk Reference for Nonprescription Drugs*, 718 (9$^{th}$ Ed., 1988).

Theragren Jr.®, made by E. R. Squibb and Sons, Inc., is a children's chewable vitamin formula. The chewable supplement contains 0.4 mg of folic acid. See *Physician's Desk Reference for Nonprescription Drugs*, 705 (9$^{th}$ Ed., 1988).

Flinstones® Complete and Bugs Bunny® Children's Chewable Vitamins, made by Miles Inc., is a children's chewable vitamins dietary supplement. These chewable supplements both contain 0.3 mg of folic acid. See *Physician's Desk Reference for Nonprescription Drugs*, 610 (9$^{th}$ Ed., 1988).

The above described folic acid compositions and methods are deficient in that they fail to provide highly absorbable folic acid. Further, the current formulations and methods do not adequately address folic acid deficiency, particularly in individuals with enhanced folic acid requirements, such as women who are pregnant.

Folic acid is poorly absorbed when it is not solubulized in the intestines. In the above described folic acid composition, the folic acid is delivered to the body in dosage forms that leave folic acid in the poorly solubilized state due to the stomach's acidic environment. As capsules and tablets are broken down by the stomach's digestive acids, the folic acid is precipitated and thus converted to a form that is less soluble. Therefore, very little folic acid in a soluble form reaches the intestines. Even the folic acid which does reach the intestines encounters problems with absorption.

As discussed above, folic acid plays an essential role in various physiological processes. Previously-available forms of folic acid do not optimize absorption of folic acid. Accordingly, it would be desirable to provide a nutritional supplement containing folic acid which overcomes the deficiencies of the previously-available folic acid supplements. In particular, there is a need for folic acid supplements which optimize or improve the absorption of folic acid.

SUMMARY OF THE INVENTION

The present invention provides improved folic acid supplements for both men and women. The present supplements overcome the deficiencies of current folic acid supplements by providing a formulation which improves or optimizes the absorption of folic acid. The supplement also provides folic acid in a highly absorbable form. The present invention is based upon the unexpected discovery that folic acid absorption is increased when folic acid is provided in a chewable or dissolvable form in combination with a non-toxic acid neutralizing compound.

Without being limited by theory, the chewing or dissolving action in this form, activates the acid neutralizing agent(s) in the mouth, thereby creating an acid neutralizing environment for the folic acid. This interaction continues as the composition moves into the stomach continuing to neutralize the digestive acids of this environment, thereby providing the preferably absorbable form of folic acid to the intestinal tract where it is absorbed into the body.

The nutritional supplements of the invention comprise stable chewable or dissolvable forms. In one embodiment of the present invention, the stable chewable or dissolvable forms include a non-toxic acid neutralizing alkaline compound combined with a folic acid compound or derivative thereof, wherein the non-toxic acid neutralizing alkaline compound has a total daily dosage of at least 2 meq of acid neutralizing capacity, and the folic acid compound or derivative thereof has a total daily dosage of at least 450 mcg.

An alternative embodiment of the invention is a nutritional supplement for optimizing or improving absorption of folic acid in an animal, which comprises a stable chewable or quickly dissolvable form including a non-toxic acid neutralizing alkaline compound surrounding a folic acid compound or derivative thereof, wherein the non-toxic acid neutralizing alkaline compound has a total daily dosage of at least 2 meq of acid neutralizing capacity, and the folic acid compound or derivative thereof has a total daily dosage of at least 450 mcg.

Another embodiment of the invention is a prenatal nutritional supplement for optimizing the absorption of folic acid in a pregnant woman and the fetus, which comprises a stable chewable or quickly dissolvable form including a non-toxic acid neutralizing alkaline compound surrounding a folic acid compound or derivative thereof, wherein the non-toxic acid neutralizing alkaline compound has a total daily dosage of at least 2 meq of acid neutralizing capacity, and the folic acid compound or derivative thereof has a total daily dosage of at least 500 mcg.

A further embodiment of the invention is a prenatal chewable nutritional supplement for optimizing absorption of folic acid in a pregnant woman, which comprises a stable chewable form comprising anon-toxic acid neutralizing alkaline compound selected from the group consisting of calcium-based compounds, antacids, aluminum-based compounds, magnesium-based compounds, sodium-based compounds, potassium-based compounds and mixtures thereof surrounding a folic acid compound or derivative thereof, wherein the non-toxic acid neutralizing alkaline compound has a total daily dosage of at least 2 meq of acid neutralizing capacity, and the folic acid compound or derivative thereof has a total daily dosage at least 50 mcg.

The present invention is also directed to a nutritional regimen for optimizing absorption of folic acid. One embodiment of the nutritional regimen comprises a stable chewable or quickly dissolvable form comprising a non-toxic acid neutralizing alkaline compound surrounding a folic acid compound or derivative thereof, wherein the non-toxic acid neutralizing alkaline compound is present in said regimen in a total daily dosage of at least 2 meq of acid neutralizing capacity, and the folic acid compound or derivative thereof is present in said regimen in a total daily dosage greater of at least 450 mcg.

An alternative embodiment of the nutritional regimen for optimizing absorption of folic acid in an animal comprises a stable chewable form comprising a non-toxic acid neutralizing alkaline compound selected from the group consisting of calcium-based compounds, antacids, aluminum-based compounds, magnesium-based compounds, sodium-based compounds, potassium-based compounds and mixtures thereof surrounding a folic acid compound or derivative thereof, wherein the non-toxic acid neutralizing alkaline compound is present in said regimen in a total daily dosage of at least 2 meq of acid neutralizing capacity, and the folic acid compound or derivative thereof has a total daily dosage of at least 450 mcg.

Another embodiment of the nutritional regimen for optimizing absorption of folic acid in a pregnant woman comprises a stable chewable form comprising a non-toxic acid neutralizing alkaline compound selected from the group consisting of calcium-based compound, antacids, aluminum-based compounds, magnesium-based compounds, sodium-based compounds, potassium-based compounds and mixtures thereof surrounding a folic acid compound or derivative thereof, wherein the non-toxic acid neutralizing alkaline compound is present in said regimen in a total daily dosage of at least 2 meq of acid neutralizing capacity, and the folic acid compound or derivative thereof has a total daily dosage of at least 500 mcg.

The present invention is also directed to methods of optimizing the absorption of folic acid in animals. In one embodiment the method of the present invention comprises administering at least once during a day to the animal a stable chewable form comprising a folic acid compound or derivative thereof in combination with a non-toxic acid neutralizing alkaline compound. The total dosage of said folic acid compound or derivative thereof administered during the day is at least 450 mcg, and the total dosage of said non-toxic acid neutralizing alkaline compound administered during the day has at least 2 meq of acid neutralizing capacity.

In an alternative embodiment, the method of optimizing folic acid absorption comprises administering at least once during a day to the animal a stable chewable form comprising a folic acid compound or derivative thereof in combination with a non-toxic acid neutralizing alkaline compound, wherein the total dosage of said folic acid compound or derivative thereof administered during the day is at least 500 mcg, and the total dosage of said non-toxic acid neutralizing alkaline compound administered during the day has at least 2 meq of acid neutralizing capacity In another embodiment, the method of optimizing the absorption of folic acid comprises administering at least once a day to a mammal a stable chewable form comprising a folic acid compound or derivative thereof in combination with a non-toxic acid neutralizing alkaline compound selected from the group consisting of calcium-based compounds, antacids, aluminum-based compounds, magnesium-based compounds, sodium-based compounds, potassium-based compounds and mixtures thereof, wherein the folic acid compound or derivative thereof has a total daily dosage of at least 500 mcg, and the non-toxic acid neutralizing alkaline compound is present in said regimen in a total daily dosage of at least 2 meq of acid neutralizing capacity.

Another objective of the present invention is to provide methods of preventing or treating folic acid deficiency in pregnant women. One embodiment of the method of preventing or treating folic acid deficiency in pregnant women comprises administering at least once during a day to the animal a stable chewable form comprising a folic acid compound or derivative thereof in combination with a non-toxic acid neutralizing alkaline compound, wherein the total dosage of said folic acid compound or derivative thereof administered during the day is at least 500 mcg, and the total dosage of said non-toxic acid neutralizing alkaline compound administered during the day has at least 2 meq of acid neutralizing capacity.

An alternative embodiment of the method of preventing or treating folic acid deficiency in an animal comprises administering at least once during a day to the animal a stable chewable form comprising a folic acid compound or derivative thereof in combination with a non-toxic acid neutralizing alkaline compound, wherein the total dosage of said folic acid compound or derivative thereof administered during the day is at least 500 mcg, and the total dosage of said non-toxic acid neutralizing alkaline compound administered during the day has at least 2 meg of acid neutralizing capacity.

In a further embodiment of the invention, a method of preventing or treating folic acid deficiency in a pregnant woman comprises administering at least once a day to the pregnant woman a stable chewable form comprising a folic acid compound or derivative thereof in combination with a non-toxic acid neutralizing alkaline compound selected from the group consisting of calcium-based compounds, antacids, aluminum-based compounds, magnesium-based compounds, sodium-based compounds, potassium-based compounds and mixtures thereof, wherein the folic acid compound or derivative thereof has a total daily dosage of at least 500 mcg, and the non-toxic acid neutralizing alkaline compound is present in said regimen in a total daily dosage of at least 2 meq of acid neutralizing capacity.

In a still further embodiment of the invention, a method of preventing or treating folic acid deficiency in a pregnant woman comprises administering at least once a day to the pregnant woman a stable chewable form comprising a folic acid compound in combination with a non-folate biologically active substance and a non-toxic acid neutralizing alkaline compound selected from the group consisting of calcium-based compounds, antacids, aluminum-based compounds, magnesium-based compounds, sodium-based compounds, potassium-based compounds and mixtures thereof, wherein the folic acid compound or derivative thereof has a total daily dosage of at least 500 mcg, and the non-toxic acid neutralizing alkaline compound is present in said regimen in a total daily dosage of at least 2 meq of acid neutralizing capacity.

In an additional embodiment of the invention, a method of preventing or treating a condition in an animal is provided which comprises administering at least once during a day to the animal a stable chewable or dissolvable form comprising a folic acid compound or derivative thereof in combination with a non-toxic acid neutralizing alkaline compound; wherein the total dosage of said folic acid compound or derivative thereof administered during the day is at least 450 mcg, and the total dosage of said non-toxic acid neutralizing alkaline compound administered during the day has at least 2 meq of acid neutralizing capacity.

DETAILED DESCRIPTION OF THE INVENTION

As used herein, "animal" refers to a human, mammal or any other animal.

"Active site" refers to the location where an active substance must be present to have its intended effect.

"Form" refers to one discrete unit containing a designated amount of the composition of the invention.

"Dissolvable form" refers to any forms which dissolve in the mouth and/or esophagus after oral ingestion.

"Chewable form" refers to any forms which are chewed in the mouth after oral ingestion.

"Acid neutralizing capacity" is the amount, in milliequivalents (meq), of an alkaline substance that will neutralize a specific amount, in milliequivalents (meq), of acid.

The present invention is based upon the unexpected discovery that greater absorption of folic acid is achieved when the folic acid is combined with a non-toxic acid neutralizing alkaline compound in a chewable or quickly dissolvable form. Without being limited by theory, one explanation for this is that the pre-wetting of the acid neutralizing alkaline compound in the mouth initiates an interaction between the folic acid compound and the non-toxic acid neutralizing alkaline compound which continues as the composition moves through the digestive system. Thus, the chewing or dissolving action in this form, activates the acid neutralizing agent(s) in the mouth, thereby creating an acid neutralizing environment for the folic acid. This interaction continues as the composition moves into the stomach continuing to neutralize the digestive acids of this environment, thereby providing the preferably absorbable form of folic acid to the intestinal tract where it is absorbed into the body. Thus, the interaction between the folic acid and non-toxic acid neutralizing alkaline compound, when administered in a chewable or dissolvable form, facilitates absorption of folic acid because a critical interaction is initiated by the chewing action or dissolving activity in the mouth.

The present invention provides an improved folic acid composition which provides a more absorbable form of folic acid. The present compositions are superior to previously-available forms of folic acid in that they result in improved folic acid absorption. In particular, the nutritional supplement of the present invention contains folic acid or a derivative thereof in combination with a non-toxic acid neutralizing compound in a chewable or dissolvable form.

The non-toxic acid neutralizing alkaline compounds for incorporation into the compositions of the present invention include, natural and synthetic alkaline compounds and compounds that react like alkaline compounds, for example, without limitation, calcium-based compounds, antacids, aluminum-based compounds, magnesium-based compounds, sodium-based compounds, potassium-based compounds, proteins, amino acids, fermented products and mixtures thereof. Further non-limiting exemplary non-toxic acid neutralizing alkaline compounds include aluminum carbonate, aluminum hydroxide, aluminum phosphate, aluminum hydroxy carbonate, aluminum citrate, dihydroaluminum sodium carbonate, aluminum magnesium glycinate, dihydroxyaluminum aminoacetate, dihydroxyaluminum aminoacetic acid, bismuth aluminate, bismuth carbonate, bismuch subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

Preferably, the compositions of the present invention contain at least 2 meq of acid neutralizing capacity of the non-toxic acid neutralizing alkaline composition. More preferably, the compositions of the present invention contain at least 5 meq of the non-toxic acid neutralizing alkaline composition. Even more preferably, the compositions of the present invention contain at least 10 meq of the non-toxic acid neutralizing alkaline composition.

For example, without limitation, when the non-toxic acid neutralizing alkaline compound is calcium carbonate, preferably, at least 100 mg of calcium carbonate is present in the composition. More preferably, the amount of calcium carbonate present is at least 200 mg. Even more preferably, the amount of calcium carbonate present is at least 250 mg. Still more preferably, the calcium carbonate present is at least 400 mg. Most preferably, the calcium carbonate present is at least 500 mg.

The compositions of the present invention include a folic acid compound or derivative thereof. The derivatives of folic acid include compounds formed from folic acid which may be structurally distinct from folic acid, but which retain the active function of folic acid. Non-limiting examples of such derivatives include salts of folic acid, alkaline salts of folic acid, esters of folic acid, chelates of folic acid and combinations thereof.

Preferably, the compositions of the present invention contain a total daily dosage of greater than 450 mcg of a folic acid compound or derivative thereof. More preferably, the compositions of the present invention contain a total daily dosage of at least 500 mcg of a folic acid compound or derivative thereof. Even more preferably, the compositions of the present invention contain a total daily dosage of at least 600 mcg of a folic acid compound or derivative thereof. Most preferably, the compositions of the present invention contain a total daily dosage of at least 1,000 mcg of a folic acid compound or derivative thereof.

The nutritional supplement is comprised of a stable chewable or dissolvable form. The form may be in any chewable or dissolvable form. Preferably, the dissolvable form will dissolve within thirty seconds of oral ingestion. Non-limiting exemplary forms of the present invention include chewable tablets, quick dissolve tablets, effervencent tablets, particulate matrices, microparticulate matrices, health bars, confections, liquids, foods, animal feeds, cereal coatings, cereals, food supplements, nutritional supplements, functional foods, nutrititive foods and mixtures thereof. The form comprises a non-toxic acid neutralizing alkaline compound combined with a folic acid compound or folic acid derivative and any necessary additive required to achieve a quick dissolve or chewable structure. The folic acid may be physically separated from the non-toxic acid neutralizing alkaline compound so that the compounds do not come into contact with one another until after ingestion.

The ability to obtain chewable or dissolvable forms is performed using well known procedures and techniques available to the ordinary skilled artisan. Each of these specific techniques or procedures for obtaining these structural characteristics do not in themselves constitute an inventive aspect of this invention.

For example, dissolvable tablets, without limitation, may prepared by combining active components with sugars and cellulose derivatives to form a uniform mixture which is then formed into compressed tablets. The compressed tablets may be formed through direct compression or granulation and then compression, without limitation. The process thus employed can provide a tablet that dissolves or disintegrates after oral administration, and generally within 30 seconds.

Chewable tablets, without limitation, may be prepared by combining various excipients, such as binders, flavorings, colorants and the like, with active components to form relatively soft, flavored, tablets that can be chewed rather than swallowed whole. Conventional tablet machinery and procedures (both direct compression and granulation) can be utilized. Chewable forms may also be prepared by molding a mixture into a shaped form, immersing the dose forms in a calcium ion bath, recovering the dose forms from the bath, rinsing the dose forms and packaging the dose forms for use. See Vellekopp et al., U.S. Pat. No. 4,765,984. The unit dose forms may be individually wrapped, packaged as multiple units on paper strips or in vials of any size, without limitation. The chewable and dissolvable tablets of the invention may be packaged in unit dose, rolls, bulk bottles, blister packs and combinations thereof, without limitation.

Health bars, without limitation, may be prepared by combining various excipients, such as binders, fillers, flavoring, colorants and the like, along with active components, and mixing to a plastic mass consistency. The mass is then either extruded or molded to form "candy bar"0 shapes that are then dried or allowed to solidify to form the final product.

Animal feeds, without limitation, may be prepared by combining active components with binding ingredients to form a plastic mass. The mass is then extruded under high pressure to form tubular (or "spaghetti-like") structures that are cut to pellet size and dried.

Cereal or cereal coatings, without limitation, may be prepared by forming the active components into pellets, flakes or other geometric shapes. The pellets, flakes or other geometric shapes are then passed under a precision spray coating device to deposit a film of active ingredients plus excipients onto the surface of the formed elements. The units thus treated are then dried or allowed to dry.

The compositions described herein are intended for administration to any animal. The compositions are preferably administered to mammals. More preferably the compositions are administered to humans. The compositions are intended to be administered to both females or male. Further, the compositions can be administered to both pregnant and non-pregnant women. Pregnant women have an enhanced need for folic acid, to prevent anemia and reduce the risks of birth defects.

The combination of the folic acid with the non-toxic acid neutralizing alkaline compound in the chewable to dissolvable forms is very effective with regard to increasing the absorption of folic acid. While it is difficult to quantify the effectiveness of the formulations. Preferably, the percentage of folic acid absorbed from an animal's gastrointestinal tract after administration of the form relative to the amount of folic acid in the chewable or dissolvable form is at least 45% depending upon intervening external or internal factors. More preferably, the percentage absorbed is at least 55%. Even more preferably, the percentage absorbed is at least 70%. Still more preferably, the percentage absorbed is at least 85%. Most preferably, the percentage absorbed is at least 95%.

Various additive may also be incorporated into the present compositions. Non-limiting examples of additives of the present invention include calcium carbonate, compressible sugar, particulate composite coating, flavorings and magnesium stearate.

The present invention also provides a prenatal nutritional supplement for optimizing the absorption of folic acid in a pregnant woman, as well as methods for optimizing absorption of folic acid and treating folic acid deficiency. Folic acid deficiency can cause anemia in the mother and birth defects in the fetus.

The invention also provides a nutritional regimen for optimizing the absorption of folic acid in pregnant women. The regimen comprises a stable chewable or quickly dissolving form comprising a non-toxic acid neutralizing alkaline compound surrounding a folic acid compound or derivative thereof, so that the folic acid compound is microencapsulated. The form is selected from the group consisting of a chewable tablet, a quick dissolve tablet, an effervescent tablet, a particular matrix, a microparticulate matrix and mixtures thereof.

The invention also provides a nutritional regimen for optimizing absorption of folic acid in an animal comprising a stable chewable from comprising a non-toxic acid neutralizing alkaline compound selected from the group consisting of calcium based compounds, antacids, aluminum-based compounds, magnesium-based compounds, sodium-based compounds, potassium-based compounds, and mixtures thereof surrounding a folic acid compound or derivative thereof. The non-toxic acid neutralizing compound has a total daily dosage of at least 2 meq of acid neutralizing capacity. The folic acid compound or derivative has a total daily dosage of greater than 450 mcg.

The method of preventing or treating folic acid deficiency in a pregnant woman comprises administering at least once during a day to the pregnant woman a stable chewable or quickly dissolvable form. The form comprises a folic acids compound or derivative thereof in combination with a non-toxic acid neutralizing alkaline compound.

The total dosage of the folic acid compound or derivative thereof administered during the day is at least 500 mcg. The total dosage of non-toxic acid neutralizing alkaline compound administered during the day is at least 2 meq of acid neutralizing capacity.

The invention also provides a method of preventing or treating folic acid deficiency in an animal. The animal can be male or a pregnant or non-pregnant female. The method comprises administering at least once during a day to the animal a stable chewable or dissolvable form. The form comprises a folic acid compound or derivative thereof in combination with a non-toxic acid neutralizing alkaline compound and a non-folate biologically active substance.

The present invention also comprises a method of preventing or treating a condition in an animal by administering the present compositions to said animal. Any physiological condition or the like could be targeted by use of the present compositions. Preferably, the condition would be a physiological condition in which folic acid is implicated, without limitation.

The present invention contemplates the use of pharmaceutically acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous material such as buffers and adsorbents in order to prepare a particular medicated compositions.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluable hydrophobic substances, such as diethyl phthalate, diethyl sebacate and caster oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

The dosage forms of the present invention may involve the administration of a nutritional composition in a single dose during a 24 hour period of time, a double dose during a 24 hour period of time, or multiple doses, e.g., more than two doses during a 24 hour period of time. The double or multiple doses may be taken simultaneously or at different times during the 24 hour period.

The compositions of the present invention are intended for use by both males and females. The dosages are adjusted according to body weight to compensate, at least partially, for differences in male and female physiological need. The compositions are particularly suitable for individuals having enhanced folic acid requirements, for example, pregnant women, without limitation. Moreover, the formulations can be further adapted based upon the specific needs, genetic predispositions or identified deficiencies of an individual.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

The following examples are illustrative of preferred embodiments of the invention and are not to be construed as limiting the invention thereto.

EXAMPLE I

Preparation of Multi-Vitamin and Mineral Supplements

The following compositions are used to prepare chewable or dissolvable folic acid supplements for administration to males or females:

TABLE I

| Component | Formula I (mg) | Formula II (mg) |
|---|---|---|
| Folic Acid | 0.45 | 1.0 |
| Calcium Carbonate | 150 | — |
| Aluminum Hydroxide | 150 | 200 |
| Compressible Sugar | 500 | 600 |
| Flavoring | 40 | 80 |
| Magnesium Stearate | 3.5 | 9 |

EXAMPLE II

The following compositions are used to prepare chewable or dissolvable folic acid supplements.

TABLE II

| Component | Ranges (mg) |
|---|---|
| Folic Acid | 0.45–1.0 |
| Calcium Carbonate | 100–1,000 |
| Aluminum Hydroxide | 150–200 |
| Compressible Sugar | 500–600 |
| Flavoring | 40–80 |
| Magnesium Stearate | 3.5–9 |

Chewable or dissolvable tablets incorporating the above formulations are prepared using conventional methods and materials known in the pharmaceutical art. The resulting folic acid supplement tablets are recovered and stored for further use.

EXAMPLE III

A chewable folic acid supplement as set forth herein may be prepared, as follows:

First, combine a compressible sugar with folic acid in a blender and blend until a uniform folic acid/sugar mixture is formed. Next, combine a flavoring, a colorant and calcium carbonate with the folic-acid/sugar mixture and blend until a uniform folic acid/calcium carbonate mixture is formed. Then, to the folic acid/calcium carbonate mixture, add magnesium stearate and blend until uniformity is attained to form a lubricated folic acid/calcium carbonate mixture. The lubricated folic acid/acid neutralizing mixture is then compressed into a tablet using conventional methods.

EXAMPLE IV

A chewable folic acid supplement as set forth herein may further be prepared, as follows:

First, combine a compressible sugar with folic acid in a blender and blend until a uniform folic acid/sugar mixture is formed. Next, add a flavoring, a colorant and aluminum hydroxide to the folic-acid/sugar mixture and blend until a uniform folic acid/aluminum hydroxide mixture is formed. Then, to the folic acid/aluminum hydroxide mixture, add magnesium stearate and blend until uniformity is attained to form a lubricated folic acid/aluminum hydroxide mixture. The lubricated folic acid/aluminum hydroxide mixture is then compressed into a tablet using conventional methods.

EXAMPLE V

A dissolvable folic acid supplement as set forth herein may be prepared, as follows:

First, combine folic acid with a compressible sugar in a blender and blend until uniformity is achieved to form a uniform compressible sugar/folic acid mixture. Next, add to the compressible sugar/folic acid mixture a coloring agent, a flavoring agent and calcium carbonate and blend until a uniform folic acid/calcium carbonate mixture is attained. Then, combine the folic acid/calcium carbonate mixture with hydroxypropylmethylcellulose and blend to form a uniform dissolvable mixture. Finally, compress the dissolvable mixture to form a tablet that will disintegrate within 30 seconds after oral ingestion.

The invention being thus described, it will be apparent that the same may be varied in many ways. Such variations are not to be regarded as a departure from the spirit and scope of the invention, and all such modifications are intended to be within the scope of the appended claims.

We claim:

1. A nutritional supplement for optimizing absorption of folic acid in an animal, which consists essentially of:
   a stable chewable, dissolvable form comprising a non-toxic acid neutralizing alkaline compound combined with a folic acid compound or derivative thereof;
   wherein the non-toxic acid neutralizing alkaline compound has a total daily dosage of at least 2 meq of acid neutralizing capacity, and the folic acid compound or derivative thereof has a total daily dosage of at least 450 mcg.

2. The nutritional supplement of claim 1, wherein said non-toxic acid neutralizing alkaline compound surrounds said folic acid compound or derivative thereof.

3. The nutritional supplement of claim 1, wherein said non-toxic acid neutralizing alkaline compound is selected from the group consisting of calcium-based compounds, antacids, aluminum-based compounds, magnesium-based compounds, sodium-based compounds, potassium-based compounds, and mixtures thereof.

4. The nutritional supplement of claim 1, wherein said non-toxic acid neutralizing alkaline compound is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

5. The nutritional supplement of claim 1, wherein said chewable or dissolvable form is selected from the group consisting of a chewable tablet, a quick dissolve tablet, an effervescent tablet, a particulate matrix, a microparticulate matrix and mixtures thereof.

6. The nutritional supplement of claim 1, wherein said folic acid compound or derivative thereof is microencapsulated.

7. The nutritional supplement of claim 1, wherein said nutritional supplement is formulated for an administration of at least once a day.

8. The nutritional supplement of claim 1, wherein said nutritional supplement is formulated for an administration of at least twice a day.

9. A nutritional supplement for optimizing absorption of a folic acid compound or derivative thereof in an animal, which consists essentially of:
   a stable chewable, dissolvable form comprising a non-toxic acid neutralizing alkaline compound surrounding a folic acid compound or derivative thereof;
   wherein the non-toxic acid neutralizing alkaline compound has a total daily dosage of at least 2 meq of acid neutralizing capacity, and the folic acid compound or derivative thereof has a total daily dosage of at least 450 mcg.

10. The nutritional supplement of claim 9, wherein said non-toxic acid neutralizing alkaline compound is selected from the group consisting of calcium-based compounds, antacids, aluminum-based compounds, magnesium-based compounds, sodium-based compounds, potassium-based compounds, and mixtures thereof.

11. The nutritional supplement of claim 9, wherein said non-toxic acid neutralizing alkaline compound is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

12. The nutritional supplement of claim 9, wherein said chewable or dissolvable form is selected from the group consisting of a chewable tablet, a quick dissolve tablet, an effervescent tablet, a particulate matrix, a microparticulate matrix and mixtures thereof.

13. The nutritional supplement of claim 9, wherein said folic acid compound or derivative thereof is microencapsulated.

14. The nutritional supplement of claim 9, wherein said nutritional supplement is formulated for an administration of at least once a day.

15. The nutritional supplement of claim 9, wherein said nutritional supplement is formulated for an administration of at least twice a day.

16. A prenatal nutritional supplement for optimizing absorption of folic acid in a pregnant woman, which consists essentially of:
   a stable chewable, dissolvable form comprising a non-toxic acid neutralizing alkaline compound surrounding a folic acid compound or derivative thereof;
   wherein the non-toxic acid neutralizing alkaline compound has a total daily dosage of at least 2 meq of acid neutralizing capacity, and the folic acid compound or derivative thereof has a total daily dosage of at least 500 mcg.

17. A method for optimizing absorption of folic acid in a pregnant woman, which comprises ingesting:
   stable chewable, dissolvable dosage form comprising a non-toxic acid neutralizing alkaline compound surrounding a folic acid compound or derivative thereof;
   wherein the non-toxic acid neutralizing alkaline compound is present in said dosage form in a total daily dosage of at least 2 meq of acid neutralizing capacity, and the folic acid compound or derivative thereof is present in said dosage form in a total daily dosage of at least 450 mcg.

18. The method of claim 17, wherein said non-toxic acid neutralizing alkaline compound is selected from the group consisting of calcium-based compounds, antacids, aluminum-based compounds, magnesium-based compounds, sodium-based compounds, potassium-based compounds, and mixtures thereof.

19. The method of claim 17, wherein said non-toxic acid neutralizing alkaline compound is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

20. The method of claim 17, wherein said chewable, dissolvable dosage form is selected from the group consisting of a chewable tablet, a quick dissolve tablet, an effervescent tablet, a particulate matrix, a microparticulate matrix and mixtures thereof.

21. The method of claim 17, wherein said folic acid compound or derivative thereof is microencapsulated.

22. The method of claim 17, wherein said dosage form is administered at least once a day.

23. The method of claim 17, wherein said dosage form is administered at least twice a day.

24. A prenatal chewable nutritional supplement for optimizing absorption of folic acid in a pregnant woman, which consists essentially of:

a stable chewable form comprising a non-toxic acid neutralizing alkaline compound selected from the group consisting of calcium-based compounds, antacids, aluminum-based compounds, magnesium-based compounds, sodium-based compounds, potassium-based compounds, and mixtures thereof surrounding a folic acid compound or derivative thereof;

wherein the non-toxic acid neutralizing alkaline compound has a total daily dosage of at least 2 meq of acid neutralizing capacity, and the folic acid compound or derivative thereof has a total daily dosage of at least 500 mcg.

25. A method for optimizing absorption of folic acid in an animal, which comprises ingesting:

stable chewable dosage form comprising a non-toxic acid neutralizing alkaline compound selected from the group consisting of calcium-based compounds, antacids, aluminum-based compounds, magnesium-based compounds, sodium-based compounds, potassium-based compounds, and mixtures thereof surrounding a folic acid compound or derivative thereof;

wherein the non-toxic acid neutralizing alkaline compound is present in said dosage form in a total daily dosage of at least 2 meq of acid neutralizing capacity, and the folic acid compound or derivative thereof is present in said dosage form in a total daily dosage of at least 450 mcg.

26. The method of claim 25, wherein said animal is a mammal.

27. The method of claim 25, wherein said animal is a pregnant female.

28. The method of claim 25, wherein said animal is a non-pregnant female.

29. The method of claim 25, wherein said animal is a male animal.

30. A method for optimizing absorption of folic acid in a pregnant woman, which comprises:

stable chewable dosage form comprising a non-toxic acid neutralizing alkaline compound selected from the group consisting of calcium-based compounds, antacids, aluminum-based compounds, magnesium-based compounds, sodium-based compounds, potassium-based compounds, and mixtures thereof surrounding a folic acid compound or derivative thereof;

wherein the non-toxic acid neutralizing alkaline compound is present in said dosage form in a total daily dosage of at least 2 meq of acid neutralizing capacity, and the folic acid compound or derivative thereof is present in said dosage form in a total daily dosage of at least 500 mcg.

31. A method of optimizing the absorption of folic acid administered to an animal in a nutritional supplement, which comprises:

administering at least once during a day to the animal a stable chewable, dissolvable form comprising a folic acid compound or derivative thereof in combination with a non-toxic acid neutralizing alkaline compound;

wherein the total dosage of said folic acid compound or derivative thereof administered during the day is at least 450 mcg, and the total dosage of said non-toxic acid neutralizing alkaline compound administered during the day has at least 2 meq of acid neutralizing capacity.

32. The method of claim 31, wherein said animal is a mammal.

33. The method of claim 31, wherein said animal is of a female gender.

34. The method of claim 31, wherein said animal is a pregnant female.

35. The method of claim 31, wherein said animal is a non-pregnant female.

36. The method of claim 31, wherein said animal is of a male gender.

37. The method of claim 31, wherein said non-toxic acid neutralizing alkaline compound is selected from the group consisting of calcium-based compounds, antacids, aluminum-based compounds, magnesium-based compounds, sodium-based compounds, potassium-based compounds, and mixtures thereof.

38. The method of claim 31, wherein said non-toxic acid neutralizing alkaline compound is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

39. The method of claim 31, wherein said chewable or dissolvable form is selected from the group consisting of a chewable tablet, a quick dissolve tablet, an effervescent tablet, a particulate matrix, a microparticulate matrix and mixtures thereof.

40. The method of claim 31, wherein said folic acid compound or derivative thereof is microencapsulated.

41. The method of claim 31, wherein said nutritional supplement is administered at least once a day.

42. The method of claim 31, wherein said nutritional supplement is administered at least twice a day.

43. A method of optimizing the absorption of folic acid administered to a pregnant woman in a nutritional supplement, which comprises:

administering at least once during a day to the pregnant woman a stable chewable, dissolvable form comprising a folic acid compound or derivative thereof in combination with a non-toxic acid neutralizing alkaline compound;

wherein the total dosage of said folic acid compound or derivative thereof administered during the day is at least 500 mcg, and the total dosage of said non-toxic acid neutralizing alkaline compound administered during the day has at least 2 meq of acid neutralizing capacity.

44. A method of preventing or treating folic acid deficiency in a pregnant woman, which comprises:

administering at least once during a day to the pregnant woman a stable chewable, dissolvable form comprising a folic acid compound or derivative thereof in combination with a non-toxic acid neutralizing alkaline compound;

wherein the total dosage of said folic acid compound or derivative thereof administered during the day is at least 500 mcg, and the total dosage of said non-toxic acid neutralizing alkaline compound administered during the day has at least 2 meq of acid neutralizing capacity.

45. A method of optimizing the absorption of folic acid administered to an animal in a nutritional supplement, which comprises:

administering at least once during a day to the mammal a stable chewable form comprising a folic acid compound or derivative thereof in combination with a non-toxic acid neutralizing alkaline compound selected from the group consisting of calcium-based compounds, antacids, aluminum-based compounds, magnesium-based compounds, sodium-based compounds, potassium-based compounds and mixtures thereof;

wherein the total dosage of said folic acid compound or derivative thereof administered during the day is at least 450 mcg, and the total dosage of said non-toxic acid neutralizing alkaline compound administered during the day has at least 2 meq of acid neutralizing capacity.

46. A method of optimizing the absorption of folic acid administered to a pregnant woman in a nutritional supplement, which comprises:

administering at least once during a day to the pregnant woman a stable chewable form comprising a folic acid compound or derivative thereof in combination with a non-toxic acid neutralizing alkaline compound selected from the group consisting of calcium-based compounds, antacids, aluminum-based compounds, magnesium-based compounds, sodium-based compounds, potassium-based compounds and mixtures thereof;

wherein the total dosage of said folic acid compound or derivative thereof administered during the day is greater than 500 mcg, and the total dosage of said non-toxic acid neutralizing alkaline compound administered during the day has at least 2 meq of acid neutralizing capacity.

47. A method of preventing or treating folic acid deficiency in a pregnant woman, which comprises:

administering at least once during a day to the pregnant woman a stable chewable form comprising a folic acid compound or derivative thereof in combination with a non-toxic acid neutralizing alkaline compound selected from the group consisting of calcium-based compounds, antacids, aluminum-based compounds, magnesium-based compounds, sodium-based compounds, potassium-based compounds and mixtures thereof;

wherein the total dosage of said folic acid compound or derivative thereof administered during the day is at least 500 mcg, and the total dosage of said non-toxic acid neutralizing alkaline compound administered during the day has at least 2 meq of acid neutralizing capacity.

48. A method of preventing or treating a condition where treatment with folic acid is indicated in an animal, which comprises:

administering at least once during a day to the animal a stable chewable, dissolvable from comprising a folic acid compound or derivative thereof in combination with a non-toxic acid neutralizing alkaline compound;

wherein the total dosage of said folic acid compound or derivative thereof administered during the day is at least 450 mcg, and the total dosage of said non-toxic acid neutralizing alkaline compound administered during the day has at least 2 meq of acid neutralizing capacity.

* * * * *

UNITED STATES PATENT AND TRADEMARK OFFICE
CERTIFICATE OF CORRECTION

PATENT NO. : 6,261,600 B1  
DATED : July 17, 2001  
INVENTOR(S) : Kirschner et al.

Page 1 of 1

It is certified that error appears in the above-identified patent and that said Letters Patent is hereby corrected as shown below:

<u>Line 41, claim 48,</u>
After "chewable dissolvable" and before "comprising a folic", please replace "from" with
-- form --.

Signed and Sealed this

Twenty-seventh Day of November, 2001

Attest:

*Nicholas P. Godici*

NICHOLAS P. GODICI
*Attesting Officer*  *Acting Director of the United States Patent and Trademark Office*